(12) United States Patent
Fukutani et al.

(10) Patent No.: US 8,396,534 B2
(45) Date of Patent: Mar. 12, 2013

(54) INTRAVITAL-INFORMATION IMAGING APPARATUS

(75) Inventors: Kazuhiko Fukutani, Yokohama (JP); Takao Nakajima, Ebina (JP); Kenichi Nagae, Kawasaki (JP); Yasuhiro Someda, Yokohama (JP); Yasufumi Asao, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 1003 days.

(21) Appl. No.: 12/130,331

(22) Filed: May 30, 2008

(65) Prior Publication Data

US 2008/0306371 A1    Dec. 11, 2008

(30) Foreign Application Priority Data

Jun. 11, 2007 (JP) ................. 2007-153587
Apr. 25, 2008 (JP) ................. 2008-115739

(51) Int. Cl.
*A61B 6/00* (2006.01)
(52) U.S. Cl. ............. 600/476; 600/438; 600/437
(58) Field of Classification Search ............ None
See application file for complete search history.

(56) References Cited

U.S. PATENT DOCUMENTS

| | | | | |
|---|---|---|---|---|
| 6,567,688 B1 | 5/2003 | Wang | | 600/430 |
| 6,608,717 B1 * | 8/2003 | Medford et al. | | 359/368 |

FOREIGN PATENT DOCUMENTS

| | | |
|---|---|---|
| EP | 2002784 A | 12/2008 |
| JP | 6-296612 | 10/1994 |
| WO | WO 2007/003700 | 1/2007 |
| WO | WO 2008/103892 | 8/2008 |

OTHER PUBLICATIONS

Oh et al, "Three-dimensional imaging of skin melanoma in vivo by dual-wavelength photoacoustic microscopy", Journal of Biomedical Optics 11(3), 034032 (May/Jun. 2006), published Jun. 14, 2006.*
M. Xu and L. V. Wang, "Photoacoustic imaging in biomedicine", Review of Scientific Instruments, 77, 041101 (2006).
R. Esenaliev et al., "Sensitivity of Laser Opto-Acoustic Imaging in Detection of Small Deeply Embedded Tumors", *IEEE Journal of Selected Topics in Quantum Electronics*, vol. 5, No. 4, Jul./Aug. 1999, pp. 981-987.
K. Köstli et al., "Optoacoustic Infrared Spectroscopy of Soft Tissue", *Journal of Applied Physics*, Aug. 2000, vol. 88, No. 3, pp. 1632-1637.
A. Oraevsky et al., "Laser Optoacoustic Imaging of Breast Cancer in vivo", *Biomedical Optoacoustics II, Proceedings of SPIE*, vol. 4256(2001) SPIE 1605-7422/01, pp. 6-15.
A. Oraevsky et al., "Laser Optoacoustic Tomography of Layered Tissues: Signal Processing", SPIE vol. 2979, 0277-786X/97, pp. 59-70.
J. Viator et al., "Depth Profiling of Absorbing Soft Materials Using Photoacoustic Methods", *IEEE Journal of Selected Topics in Quantum Electronics*, vol. 5, No. 4, Jul./Aug. 1999, pp. 989-996.

* cited by examiner

*Primary Examiner* — Long V. Le
*Assistant Examiner* — Nicholas Evoy
(74) *Attorney, Agent, or Firm* — Fitzpatrick, Cella, Harper & Scinto

(57) ABSTRACT

An intravital-information imaging apparatus includes light sources for irradiating a living body with light, and acoustic-wave detectors that detect acoustic waves generated from a light absorber having absorbed part of energy of the light from the light sources, the light absorber existing in the living body. Furthermore, the intravital-information imaging apparatus includes signal processors that calculate information representing a distribution of optical characteristic values of the living body using sound pressures of the acoustic waves generated from the light absorber.

6 Claims, 5 Drawing Sheets

INTRAVITAL-INFORMATION IMAGING APPARATUS

BACKGROUND OF THE INVENTION

1. Field of the Invention

The present invention relates to intravital-information imaging apparatuses.

2. Description of the Related Art

Generally, many imaging apparatuses that employ X-rays, ultrasound, or magnetic resonance imaging (MRI) are used in the medical field.

Furthermore, in the medical field, research is being conducted for optical imaging apparatuses for obtaining intravital information by irradiating a living body with light from a light source, such as a laser, so that the light propagates in the living body, and detecting the propagated light or the like.

As a type of optical imaging technique, photoacoustic tomography (PAT) has been proposed. Photoacoustic tomography is described, for example, in M. Xu and L. V. Wang, "Photoacoustic imaging in biomedicine", Review of Scientific Instruments, 77, 041101 (2006).

In photoacoustic tomography, a living body is irradiated with pulsed light emitted from a light source, an acoustic wave generated from a biological tissue having absorbed the energy of light propagated and diffused in the living body is detected at multiple points, and corresponding signals are analyzed to form a visual image representing intravital information. This makes it possible to obtain a distribution of optical characteristic values in the living body, particularly, a distribution of optical-energy absorption densities.

According to the reference mentioned above, in photoacoustic tomography, the sound pressure (P) of an acoustic wave generated from a light absorber in a living body in response to absorbed light can be expressed by equation (1) below:

$$P = \Gamma \cdot \mu_a \cdot \Phi \quad (1)$$

where $\Gamma$ denotes the Grüneisen coefficient, which is a value of elasticity characteristic determined by dividing the product of the thermal coefficient of volume expansion or isobaric volume expansion coefficient ($\beta$) and the square of the speed of light (c) by the specific heat at constant pressure ($C_p$).

$\mu_a$ denotes the absorption coefficient of the light absorber, and $\Phi$ denotes the amount of local light indicating the optical fluence (light with which the light absorber is irradiated).

Since it is known that $\Gamma$ is substantially constant for a specific tissue, the distribution of the products of $\mu_a$ and $\Phi$, i.e., the distribution of optical-energy absorption densities, can be obtained by measuring change in sound pressure P representing the magnitude of the acoustic wave at multiple points by time division.

In the photoacoustic tomography according to the related art described above, as will be understood from equation (1), in order to obtain a distribution of absorption coefficients ($\mu_a$) in a living body from a measurement of change in sound pressure (P), it is necessary to obtain by some method the distribution of the local amounts of light with which a light absorber is irradiated. However, since light introduced in a living body is diffused, it is difficult to estimate the local amount of light with which the light absorber is irradiated. Thus, with ordinary measurement of sound pressures of a generated acoustic wave alone, it is only possible to make an image representing a distribution of optical-energy absorption densities ($\mu_a \times \Phi$).

That is, it is difficult to calculate a distribution of the amounts of light with which the light absorber is irradiated ($\Phi$) and to accurately separate and generate an image of a distribution of absorption coefficients ($\mu_a$) in a living body on the basis of a measurement of sound pressures of an acoustic wave.

As a result, it is difficult to accurately identify constituents of biological tissues or to measure density on the basis of the distribution of absorption coefficients ($\mu_a$) in a living body.

SUMMARY OF THE INVENTION

The present invention provides an intravital-information imaging apparatus with which it is possible to obtain a high-resolution distribution of optical characteristic values in a living body, particularly a distribution of optical absorption coefficients, or an average effective attenuation coefficient of a living body.

With the intravital-information imaging apparatus according to the present invention, it is possible to obtain a high-resolution distribution of optical characteristic values in a living body, particularly a distribution of optical absorption coefficients, or an average effective attenuation coefficient of a living body, and to generate images accurately representing such information.

Further features of the present invention will become apparent from the following description of exemplary embodiments with reference to the attached drawings.

DESCRIPTION OF THE EMBODIMENTS

Now, embodiments of the present invention will be described with reference to the drawings.

First Embodiment

Figure 1A:
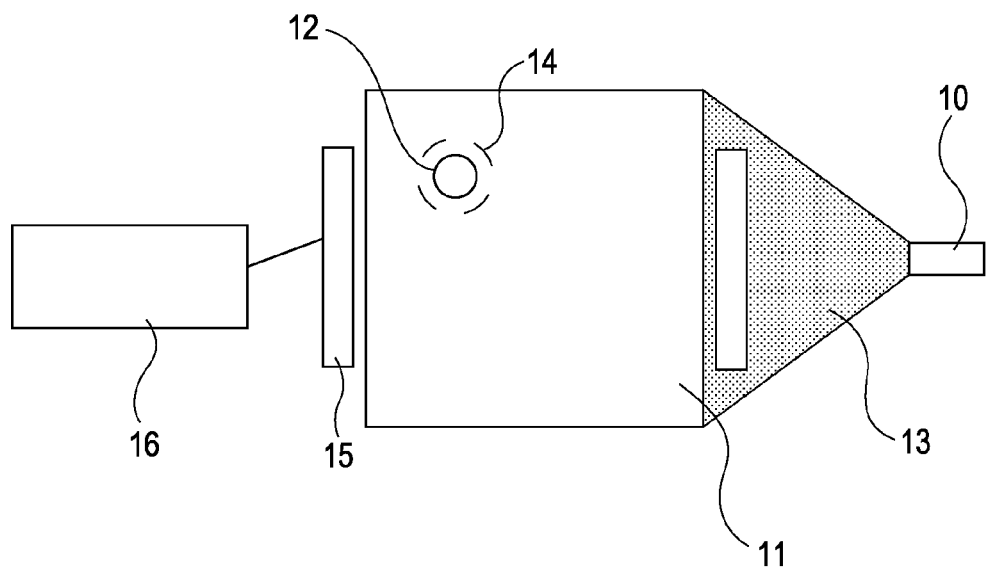
FIGS. 1A and 1B are diagrams showing an example of the configuration of an intravital-information imaging apparatus according to a first embodiment of the present invention.
Figure 1B:
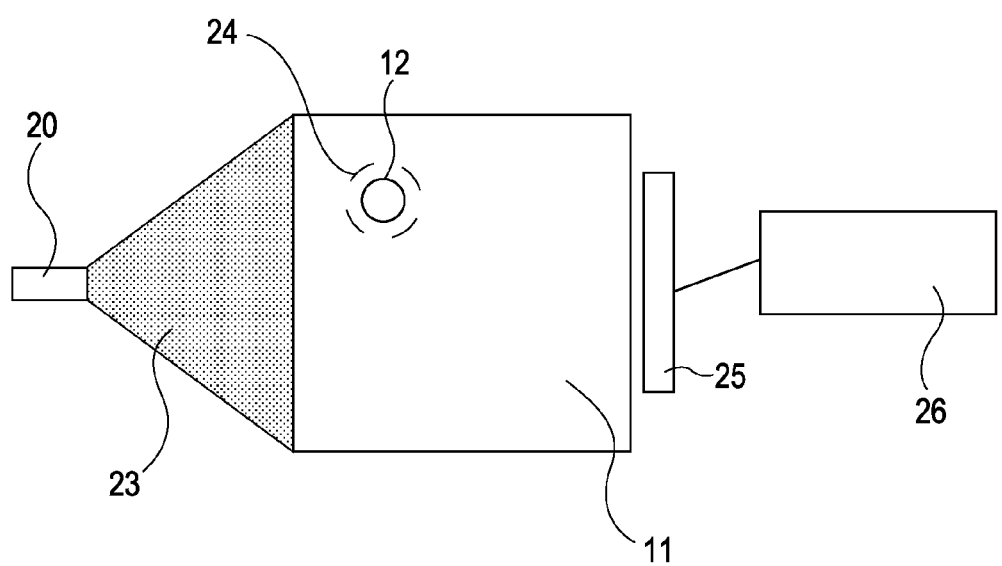

FIGS. 1A and 1B show an example of the configuration of an intravital-information imaging apparatus according to a first embodiment.

Referring to FIG. 1A, when a living body 11 is irradiated with pulsed light 13 from a first light source 10, an acoustic wave 14 is generated from a light absorber 12 inside the living body 11. The acoustic wave 14 is detected by an acoustic-wave detector 15 in the form of an electric signal. The detected electric signal is analyzed by a signal processor 16.

The initial sound pressure $P_1$ of the acoustic wave 14 generated from the light absorber 12 in the living body 11 when the living body 11 is irradiated with the pulsed light 13 from the first light source 10 can be expressed by equation (2) below:

$$P_1 = \Gamma \cdot \mu_a \cdot \Phi = \Gamma \cdot \mu_a \cdot \Phi_0 \cdot \exp(-\mu_{eff} \cdot d_1) \quad (2)$$

where $\Gamma$ denotes the Grüneisen coefficient of the light absorber 12, $\mu_a$ denotes the absorption coefficient of the light absorber 12, $\Phi$ denotes the amount of local light absorbed by the light absorber 12, $\mu_{eff}$ denotes an average effective attenuation coefficient of the living body 11, and $\Phi_0$ denotes the amount of light that irradiates the surface of the living body 11 from the first light source 10.

Furthermore, $d_1$ denotes the distance (first distance) from a region where the living body 11 is irradiated with the pulsed light 13 from the first light source 10 (irradiation region) to the light absorber 12, i.e., the depth.

Assuming that the Grüneisen coefficient ($\Gamma$) of the light absorber 12 is known since the Grüneisen coefficient ($\Gamma$) for a specific tissue of the body is substantially constant, through time-resolved measurement of the sound pressure (P) by the acoustic-wave detector 15, it is possible to find the distribution of acoustic-wave generating sources and the distribution of the products of the absorption coefficient ($\mu_a$) and the amount of light ($\Phi$) (the distribution of optical-energy absorption densities).

It is assumed here that the amount of light $\Phi_0$ from each of the light sources with which the living body 11 is irradiated is constant, and that light propagates through the living body 11 like a plane wave since a region that is large enough in relation to the thickness of the living body 11 is irradiated with light. The amount of light $\Phi_0$ with which the living body 11 is irradiated can be maintained constant by emitting a constant amount of light from the light source.

Furthermore, by performing time-resolved measurement of change in sound pressure (P) at multiple points, it is possible to estimate the distribution of acoustic-wave generating sources or the distribution of optical-energy absorption densities.

Referring next to FIG. 1B, the living body 11 is irradiated with pulsed light 23 from a second light source 20, which is provided at a position different from the position of the first light source 10. In this case, assuming that the light absorber 12 is not located at the center of the living body 11, the distance between the irradiation region of the living body 11 and the light absorber 12 differs between the first light source 10 and the second light source 20.

When the living body 11 is irradiated with the pulsed light 23, an acoustic wave 24 is generated from the light absorber 12 inside the living body 11. The acoustic wave 24 is detected by an acoustic-wave detector 25 in the form of an electric signal. The detected electric signal is processed by a signal processor 26.

The initial sound pressure $P_2$ of the acoustic wave 24 generated from the light absorber 12 in response to the pulsed light 23 emitted from the second light source 20, whose distance from the light absorber 12 inside the living body 11 differs from that of the first light source 10, can be expressed by equation (3) below:

$$P_2 = \Gamma \cdot \mu_a \cdot \Phi = \Gamma \cdot \mu_a \cdot \Phi_0 \cdot \exp(-\mu_{eff} \cdot d_2) \quad (3)$$

where $d_2$ denotes the distance (second distance) from a region where the living body 11 is irradiated with the pulsed light 23 from the second light source 20 to the light absorber 12, i.e., the depth. As described earlier, it is possible to estimate the distribution of acoustic-wave generating sources or the distribution of optical-energy absorption densities through time-resolved measurement of change in sound pressure (P).

Taking the logarithm of both sides of equation (2) yields equation (4) below:

$$\mathrm{Log}(P_1) = \mathrm{Log}(\Gamma \cdot \mu_a \cdot \Phi_0) - \mu_{eff} \cdot d_1 \quad (4)$$

Furthermore, taking the logarithm of both sides of equation (3) yields equation (5) below:

$$\mathrm{Log}(P_2) = \mathrm{Log}(\Gamma \cdot \mu_a \cdot \Phi_0) - \mu_{eff} \cdot d_2 \quad (5)$$

The sound pressures $P_1$ and $P_2$ can be determined from measured values. Furthermore, the first distance $d_1$ and the second distance $d_2$ can be determined through time-resolved measurement of sound pressures.

Figure 2:
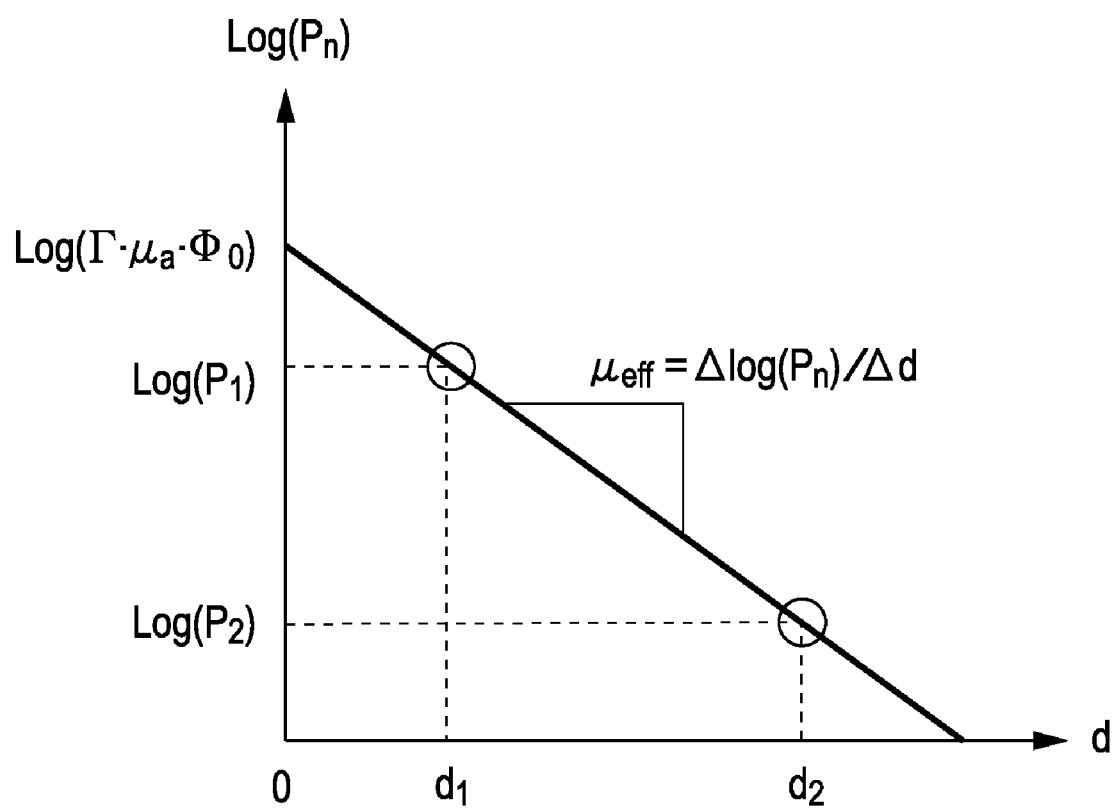
FIG. 2 is a diagram showing an example of the result of analyzing signals obtained by the intravital-information imaging apparatus according to the first embodiment of the present invention.

FIG. 2 shows a graph in which the horizontal axis represents a distance d between a region where the living body 11 is irradiated with light and the light absorber 12 in the living body 11, the vertical axis represents the logarithm of the sound pressure of the resulting acoustic wave, and points are plotted using these values as coordinate values.

By identifying a straight line on the basis of the coordinate values in FIG. 2 by the least square method or the like, it is possible to obtain an average effective attenuation coefficient ($\mu_{eff}$) of the living body 11 from the slope of the straight line.

By obtaining the average effective attenuation coefficient ($\mu_{eff}$) of the living body 11 as described above, as will be understood from equation (2), it is possible to obtain the amount of light $\Phi$ with which the light absorber 12 is irradiated. Accordingly, it is possible to convert the distribution of optical-energy absorption densities, which are the products of the absorption coefficients ($\mu_a$) and the amounts of light ($\Phi$), into a distribution of absorption coefficients. Furthermore, it becomes possible to accurately identify the constituents of biological tissues or to accurately measure density on the basis of the distribution of absorption coefficients in the living body 11, which has been difficult with existing techniques of photoacoustic tomography.

The method of calculation described above is only an example, and without limitation to the specific method, the point of the present invention is to calculate information representing a distribution of optical characteristic values of a living body using relative position information of a light absorber and an irradiation region and the sound pressure of an acoustic wave generated from the light absorber. That is, any method of calculation can be used as long as it is possible to calculate an average effective attenuation coefficient ($\mu_{eff}$) of a living body.

For example, in the embodiment, the regions of irradiation with light from light sources are varied to detect sound pressures in cases where the distances between the irradiation regions and a light absorber are varied, the logarithms of the detected sound pressures are plotted in relation to the distances, and an effective attenuation coefficient is obtained from the slope of the plotted points. Alternatively, it is possible to obtain an effective attenuation coefficient by directly finding a change curve that fits the exponential function according to equation (2) or (3) without taking the logarithms of sound pressures. As described above, it is possible to obtain an effective attenuation coefficient in various ways.

Next, the embodiment will be described in more detail.

Each of the first light source 10 and the second light source 20 emits pulsed light having a specific wavelength such that the light is absorbed in the light absorber 12 introduced in the living body 11. It is desired that the pulsed light is such light that satisfies stress confinement conditions.

Lasers can be used as these light sources. Alternatively, for example, diodes can be used instead of lasers. As lasers, various types of lasers can be used, such as solid-state lasers, gas lasers, dye lasers, or semiconductor lasers.

In this embodiment, in order to measure the distribution of light absorption coefficients having wavelength dependence, it is possible to use light sources that are capable of emitting light having different wavelengths instead of light having a single wavelength.

In this case, for example, dye lasers or OPO (optical parametric oscillator) lasers that can change the wavelength of light that is emitted can be used.

For example, the wavelengths of light emitted from the light sources are in a range of 700 nm to 1100 nm, in which absorption that occurs in living bodies is small.

In the case where a distribution of optical characteristic values of a biological tissue in a region relatively close to the surface of a living body is to be obtained, it is possible to use a wider wavelength range than the above wavelength range, such as a wavelength range of 400 nm to 1600 nm.

If it is not possible to arrange the light sources in the proximity of a living body as a subject, it is possible to guide an irradiating portion to a living body using an optical guide system, such as an optical fiber.

In the embodiment described with reference to FIGS. 1A and 1B, two light sources, namely, the first light source 10 and the second light source 20, are used. Alternatively, data of acoustic waves may be measured using a single light source by emitting light from different positions using an optical-path converter, such as a mirror. That is, information representing a distribution of optical characteristic values may be calculated from relative position information obtained based on a first distance corresponding to a first position from which light is emitted and a second distance corresponding to a second position from which light is emitted, different from the first position.

Furthermore, by measuring data of acoustic waves using three or more light sources, it is possible to obtain coordinate values of a larger number of points. This is beneficial in that a more accurate value can be obtained.

In this embodiment, the acoustic-wave detectors 15 and 25 detect the acoustic waves 14 and 24 generated from the light absorber 12 in the living body 11, having absorbed parts of energy of light from the light sources 10 and 20 with which the living body 11 is irradiated, and converts the acoustic waves 14 and 24 into electric signals. As the acoustic-wave detectors 15 and 25, any type of acoustic-wave detectors capable of detecting acoustic-wave signals may be used, such as transducers based on piezoelectric effects, transducers based on optical oscillation, or transducers based on capacitance change.

In the embodiment described with reference to FIGS. 1A and 1B, two acoustic-wave detectors are provided individually in association with two light sources. Alternatively, acoustic waves generated in response to irradiation by two light sources may be detected by a single acoustic-wave detector.

If the amplitudes of the electric signals obtained by the acoustic-wave detectors are small, the signals may be amplified.

Between the acoustic-wave detectors and a tissue of a living body as a subject, an acoustic impedance matching medium may be provided to suppress reflection of acoustic waves.

In this embodiment, the signal processors 16 and 26 are capable of analyzing electric signals supplied from the acoustic-wave detectors 15 and 25 to obtain information representing a distribution of optical characteristic values of the living body 11. More specifically, it is possible to obtain a distribution of optical-energy absorption densities, a distribution of light absorption characteristic values, an average effective attenuation coefficient, or the like.

Without limitation, however, any type of signal processors that are capable of storing intensities of acoustic waves and temporal change thereof and converting the data into data representing a distribution of optical characteristic values through calculation may be used.

For example, an oscilloscope and a computer capable of analyzing data stored in the oscilloscope may be used.

Furthermore, although two signal processors are provided in the embodiment described with reference to FIGS. 1A and 1B for convenience of description, information representing a distribution of optical characteristic values may be calculated by a single signal processor or three or more signal processors.

If a light source is capable of emitting light having different wavelengths and a living body is irradiated with the light with different wavelengths, it is possible to generate an image representing a distribution of densities of constituents of the living body using a distribution of optical characteristic values in the living body that vary depending on the individual wavelengths.

For example, it is possible to generate an image representing a distribution of densities of constituents of a living body by calculating a distribution of absorption coefficients and comparing their values with the wavelength dependency specific to each of the constituents of biological tissues (glucose, collagen, oxidized or reduced hemoglobin, and so forth).

The light absorber 12 exists inside the living body 11 and absorbs light. For example, the light absorber 12 may be tumors, blood vessels, or other tissues of the living body 11. When a molecular probe is used as the light absorber 12, generally, for example, indocyanine green (ICG) is used. However, any material may be used as long as the material generates a stronger acoustic wave than surrounding intravital constituents when irradiated with pulsed light.

By using such an intravital-information imaging apparatus, it is possible to generate an image representing a distribution of optical characteristics of the molecular probe introduced in a living body more accurately and readily than the related art.

Second Embodiment

In a second embodiment, a distribution of optical characteristic values is calculated from information representing a temporal change in sound pressures, obtained by simultaneous irradiation by a plurality of light sources.

Figure 3:
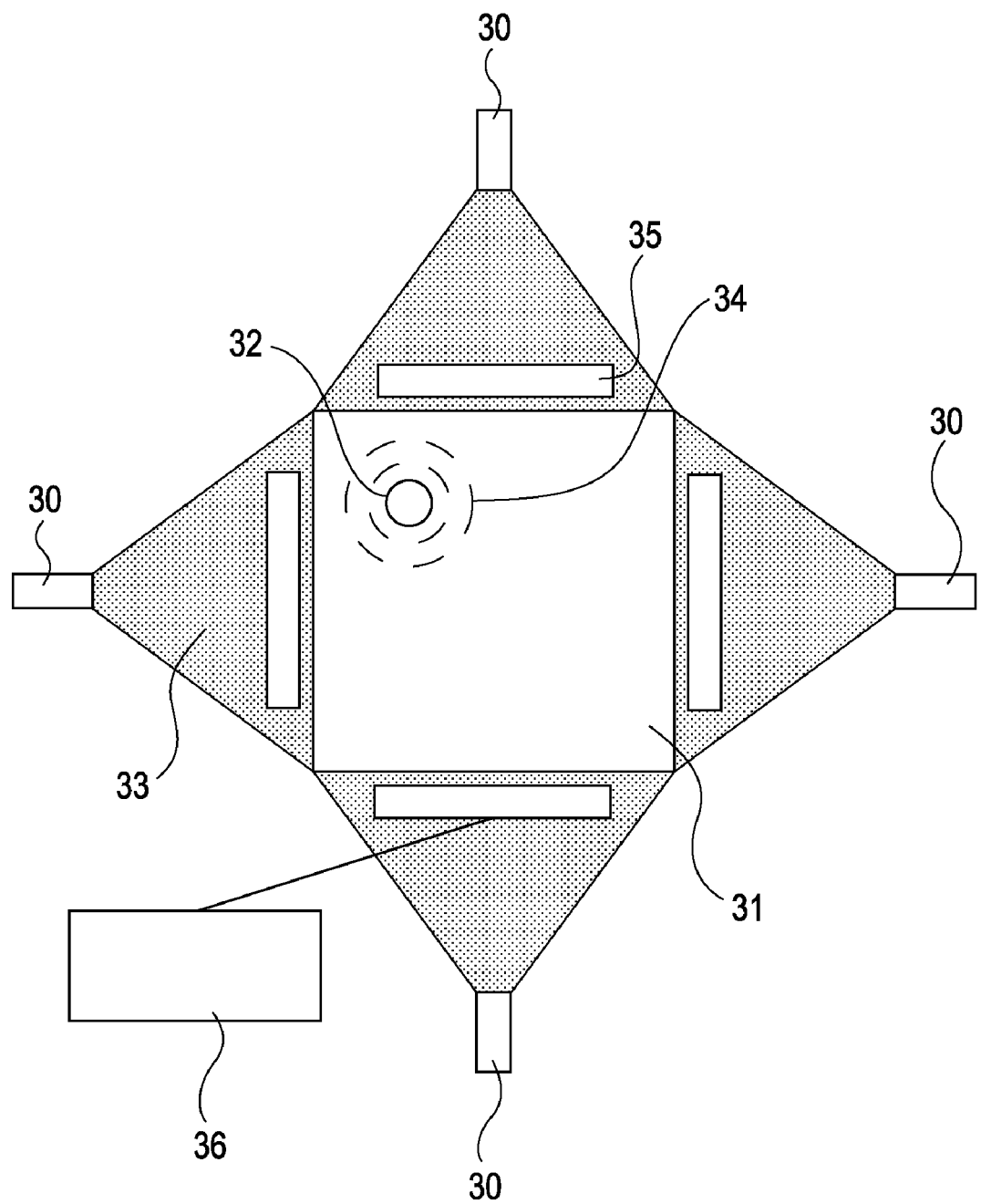
FIG. 3 is a diagram showing an example of the configuration of an intravital-information imaging apparatus according to a second embodiment of the present invention.

FIG. 3 shows an example of the configuration of an intravital-information imaging apparatus according to the second embodiment.

In FIG. 3, 30 denotes light sources, 31 denotes a living body, 32 denotes a light absorber, 33 denotes pulsed light, 34 denotes an acoustic wave, 35 denotes acoustic-wave detectors, and 36 denotes a signal processor (information processor).

When the living body 31 is irradiated with the pulsed light 33 spreading from the n (e.g., four in FIG. 3) light sources 30, the sound pressure $P_{total}$ of the acoustic wave 34 generated from the light absorber 32 inside the living body 31 can be expressed by equation (6) below:

$$P_{total} = \Gamma \cdot \mu_a \cdot \Phi = \Gamma \cdot \mu_a \cdot \sum_{i=1}^{n} \Phi_0 \cdot \exp(-\mu_{\mathit{eff}} \cdot d_i) \quad (6)$$

where $\Gamma$ denotes the Grüneisen coefficient of the light absorber 32, $\mu_a$ denotes the absorption coefficient of the light absorber 32, Φ denotes the amount of local light absorbed by the light absorber 32, $\mu_{eff}$ denotes an average effective attenuation coefficient of the living body 31, and $\Phi_0$ denotes the amount of light that enters the living body 31 from the light sources 30.

Furthermore, $d_i$ denotes the distance from a region where the living body 31 is irradiated with the pulsed light 33 from the i-th light source 30 to the light absorber 32.

Assuming that the Grüneisen coefficient (Γ) of the light absorber 32 is known since the Grüneisen coefficient (Γ) for a specific tissue of the body is substantially constant, through time-resolved measurement of the sound pressure (P) by the acoustic-wave detectors 35, it is possible to find the distribution of first acoustic-wave generating sources and the distribution of the products of the absorption coefficients ($\mu_a$) and the amounts of light (Φ) (the distribution of first optical-energy absorption densities).

It is assumed here that the amount of light $\Phi_0$ from each of the light sources is constant, and that light propagates through the living body 31 like a plane wave.

Figure 4:
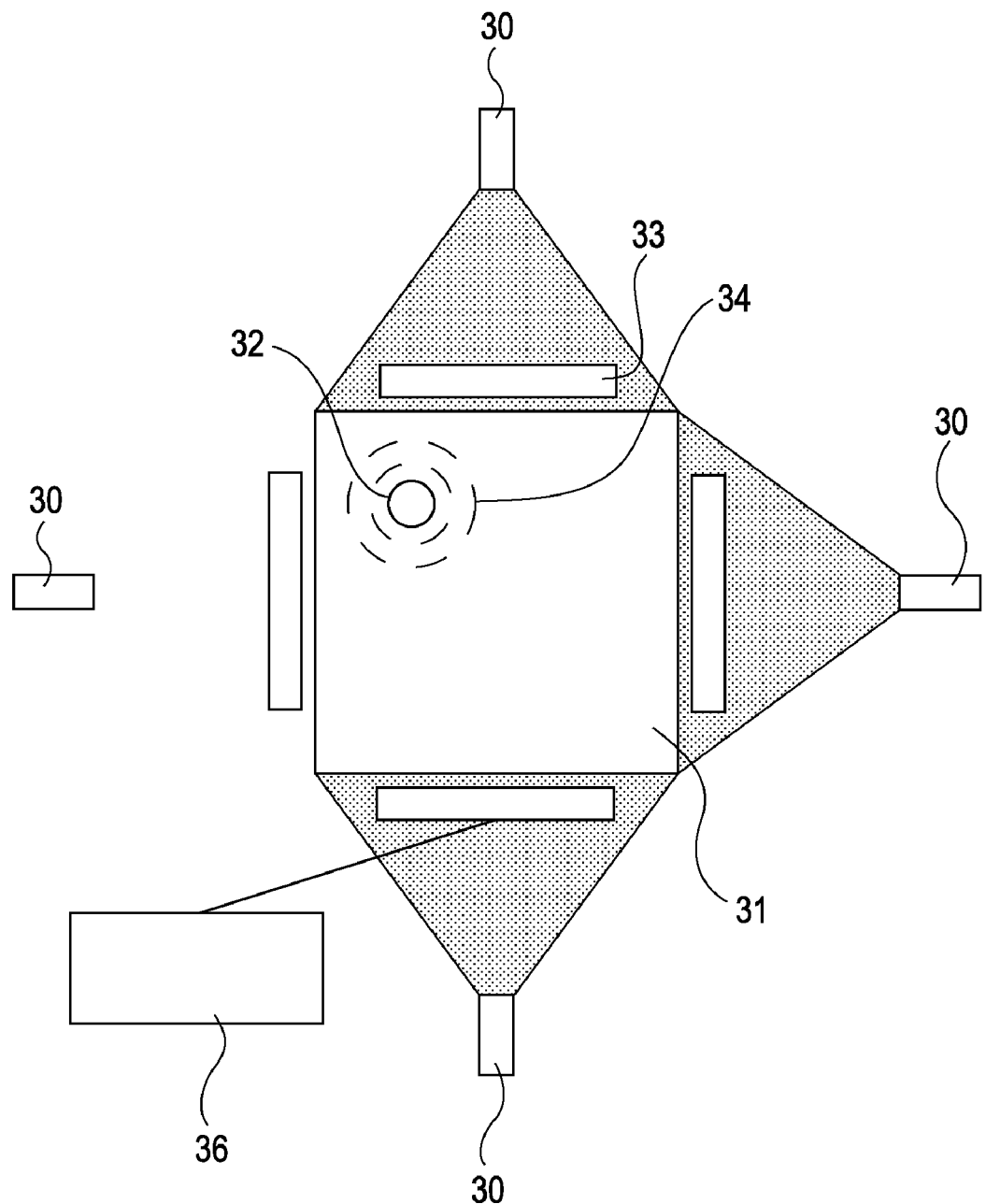
FIG. 4 is a diagram showing a state in the second embodiment of the present invention, where light from one or more light sources is blocked and a living body is simultaneously irradiated with light from the other light sources, and an acoustic wave generated from a light absorber is detected.

When light from the k-th light source among the light sources 30 is blocked as shown in FIG. 4, the living body 31 is irradiated with pulsed light from the other (n−1) light sources 30. The sound pressure $P_k$ of an acoustic wave generated from the light absorber 32 in response to the pulsed light can be expressed by equation (7) below:

$$P_k = \Gamma \cdot \mu_a \cdot \Phi \quad (7)$$

$$= \Gamma \cdot \mu_a \cdot \sum_{i=1}^{n} \Phi_0 \cdot \exp(-\mu_{eff} \cdot d_i) - \Gamma \cdot \mu_a \cdot \Phi_0 \cdot \exp(-\mu_{eff} \cdot d_k)$$

where $d_k$ denotes the distance from a region where the living body 31 is irradiated with the pulsed light 33 from the k-th light source 30 to the light absorber 32.

Through time-resolved measurement of change in sound pressure (P), it is possible to obtain a distribution of second acoustic-wave generating sources or a distribution of second optical-energy absorption densities.

The differences between sound pressures obtained with n light sources and sound pressures obtained with n−1 light sources can be obtained by subtracting equation (7) from equation (6), and can be expressed by equation (8) below:

$$P_{total} - P_k = \Gamma \cdot \mu_a \cdot \Phi_0 \cdot \exp(-\mu_{eff} \cdot d_k) \quad (8)$$

Taking the logarithms of both sides of equation (8) yields equation (9) below:

$$\text{Log}(P_{total} - P_k) = \text{Log}(\Gamma \cdot \mu_a \cdot \Phi_0) - \mu_{eff} \cdot d_k \quad (9)$$

Figure 5:
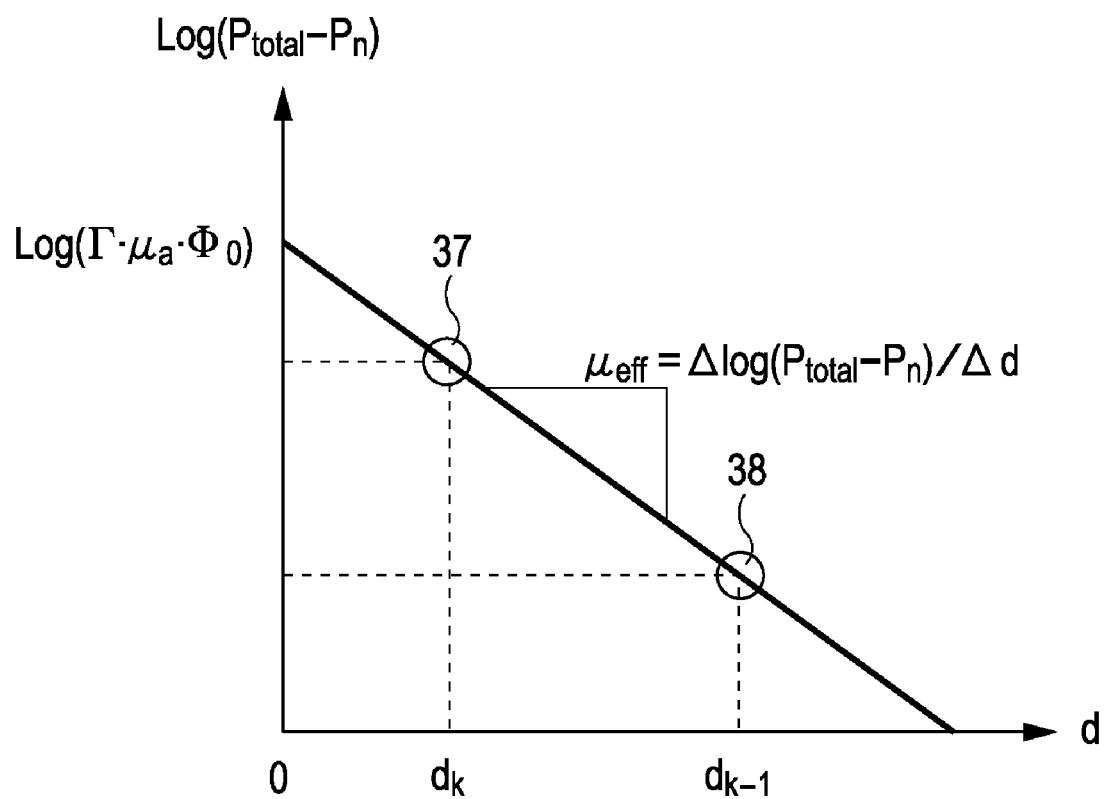
FIG. 5 is a diagram showing an example of the result of analyzing signals obtained by the intravital-information imaging apparatus according to the second embodiment of the present invention.

The left side of equation (9) can be determined from measured values of sound pressures. The distance $d_k$ between a region of the living body 31 irradiated with light from the k-th blocked light source and the light absorber 32 can be determined through time-resolved measurement of sound pressures. Thus, using the distance d between the irradiation region and the light absorber 32 as the horizontal axis and the logarithm of the sound pressure of the acoustic wave as the vertical axis, a point having these values as coordinate values can be plotted as indicated by reference numeral 37 in FIG. 5.

Similarly, when light from the (k−1)-th light source is blocked, the living body 31 is irradiated with pulsed light from n−2 light sources, and an acoustic wave $P_{k-1}$ generated from the light absorber 32 is measured. Then, by obtaining the difference between the acoustic wave $P_k$ and the acoustic wave $P_{k-1}$ and the distance $d_{k-1}$ between the region where the living body 31 is irradiated with light from the blocked (k−1)-th light source and the light absorber 32, a point can be plotted as indicated by reference numeral 38 in FIG. 5.

For example, by taking the difference between data obtained by irradiation with light from the first, second, and third (three) light sources and data obtained by irradiation with light from the first and second (two) light sources, a point can be plotted as indicated by reference numeral 37. Furthermore, by taking the difference between the data obtained by irradiation with light from the first and second (two) light sources and data obtained by irradiation with light from the first (one) light source, a point can be plotted as indicated by reference numeral 38.

Alternatively, it is possible to plot a point based on the difference between the data obtained by irradiation with light from the first and second (two) light sources and data obtained by irradiation with light from the first (one) light source, and then plot another point based on the data obtained by irradiation with light from the first light source. That is, in this embodiment, it suffices to provide at least two light sources.

By identifying a straight line by the least square method or the like on the basis of the coordinate values of the points plotted as described above and as shown in FIG. 5, it is possible to obtain an effective attenuation coefficient of the living body 31 on the basis of the slope of the straight line.

By obtaining the average effective attenuation coefficient ($\mu_{eff}$) of the living body 11 as described above, as will be understood from equation (2), it is possible to obtain the amount of light Φ with which the light absorber 12 is irradiated. Accordingly, it is possible to convert the distribution of optical-energy absorption densities, which are the products of the absorption coefficients ($\mu_a$) and the amounts of light (Φ), into a distribution of absorption coefficients. Furthermore, it becomes possible to accurately identify the constituents of biological tissues or to accurately measure density on the basis of the distribution of absorption coefficients in the living body 11, which has been difficult with existing techniques of photoacoustic tomography.

The method of calculation described above is only an example, and without limitation to the specific method, the point of the present invention is to calculate information representing a distribution of optical characteristic values of a living body using relative position information or difference in sound pressure obtained from an acoustic wave generated from a light absorber. That is, any method of calculation can be used as long as it is possible to calculate an average effective attenuation coefficient ($\mu_{eff}$) of a living body.

For example, it is possible to obtain an effective attenuation coefficient by directly finding a change curve that fits the exponential function according to equation (8) or (3) without taking the logarithms of changes in sound pressures. As described above, it is possible to obtain an effective attenuation coefficient in various ways.

Next, the embodiment will be described in more detail.

The light sources 30 irradiate the living body 31 with the pulsed light 33, and are provided at multiple positions so that different regions of the living body 31 can be irradiated simultaneously. Furthermore, it is allowed to block light from at least two light sources. Light can be blocked by turning the light sources 30 ON or OFF, or by providing light blocking parts between the light sources 30 and the living body 31.

As the light sources 30, the types of light sources described in relation to the first embodiment can be used.

The light absorber 32 exists in the living body 31 and absorbs light. For example, the light absorber 32 may be tumors, blood vessels, or other tissues in the living body 31.

The light absorber 32 absorbs part of energy of the pulsed light 33 to generate the acoustic wave 34.

The acoustic-wave detectors 35 detects the acoustic waves 34 generated by the light absorber 32 having absorbed part of the energy of the pulsed light 33, and converts the acoustic wave 34 into an electric signal.

Although a plurality of acoustic-wave detectors are provided in the proximity of the surface of a living body, without limitation, other arrangements are possible as long as it is possible to detect an acoustic wave at multiple points.

That is, since the same effect can be achieved as long as it is possible to detect an acoustic wave at multiple points, the surface of a living body may be scanned two-dimensionally using a single acoustic-wave detector.

Furthermore, each acoustic-wave detector may be an array in which detectors are arrayed one-dimensionally or two-dimensionally.

Furthermore, an amplifier or an acoustic impedance matching agent, described in relation to the first embodiment, may be used.

The signal processor 36 analyzes the electric signal from the acoustic-wave detectors to obtain information representing a distribution of optical characteristic values of the living body 31. More specifically, it is possible to obtain a distribution of optical-energy absorption densities, a distribution of optical absorption characteristic values, an average effective attenuation coefficient, or the like.

As described in relation to the first embodiment, if light source is capable of emitting light having different wavelengths and a living body is irradiated with the light with different wavelengths, it is possible to generate an image representing a distribution of densities of constituents of the living body using a distribution of optical characteristic values in the living body that vary depending on the individual wavelengths.

According to the second embodiment, by simultaneous irradiation with light from a plurality of light sources, it is possible to increase the amount of light with which the light absorber 32 in the living body 31 is irradiated. Thus, compared with the related art, an acoustic wave signal having a greater magnitude can be obtained. Furthermore, by using difference information of measurement results, it is possible to reduce noise, for example, the effect of diffusion, reflection, or the like of the acoustic wave in the living body 31. Accordingly, the distribution of optical characteristic values in the living body 31 becomes insusceptible to measurement noise, so that accurate analysis can be achieved.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

This application claims the benefit of Japanese Application No. 2007-153587 filed Jun. 11, 2007 and No. 2008-115739 filed Apr. 25, 2008, which are hereby incorporated by reference herein in their entirety.

What is claimed is:

1. An intravital-information imaging apparatus that performs imaging using an acoustic wave generated by irradiating a subject with light, the intravital-information imaging apparatus comprising:
   a light source configured to irradiate the subject with light;
   an acoustic-wave detector configured to detect an acoustic wave generated from a light absorber that has absorbed a part of energy of the light from said light source, the light absorber existing inside the subject; and
   a signal processor configured to calculate an average effective attenuation coefficient of the subject using relative-position information representing a relative position between the light absorber and an irradiation region of the subject and sound pressures of the acoustic wave, the relative-position information and the sound pressures being obtained by analyzing electric signals corresponding to the acoustic wave detected by said acoustic-wave detector.

2. The intravital-information imaging apparatus according to claim 1, wherein said light source includes two or more light sources, and said signal processor is further configured to calculate the average effective attenuation coefficient using a first distance, which is a distance measured from a first one of said light sources, and a second distance, which is a distance measured from a second one of said light sources, said first and second light sources being provided at mutually different positions.

3. The intravital-information imaging apparatus according to claim 1, further comprising an optical-path converter configured to convert an optical path of the light from said light source, wherein said signal processor is further configured to calculate the average effective attenuation coefficient using a first distance, which is a distance measured from a first position, and a second distance, which is a distance measured from a second position, the second position being varied from the first position by said optical-path converter.

4. The intravital-information imaging apparatus according to claim 1, wherein said light source includes two or more light sources, and said signal processor is further configured to calculate the average effective attenuation coefficient using differences between sound pressures obtained by simultaneous irradiation with light from n light sources and sound pressures obtained by simultaneous irradiation with light from n−1 light sources.

5. The intravital-information imaging apparatus according to claim 1, wherein said signal processor is further configured to calculate an average effective attenuation coefficient of the living body using a straight line identified on the basis of coordinate values represented by the relative-position information and logarithms of the sound pressures of the acoustic wave generated from the light absorber.

6. The intravital-information imaging apparatus according to claim 5, wherein the straight line is identified using the least square method on the basis of the coordinate values.

* * * * *